United States Patent
Govari (10) Patent No.: US 12,114,920 B2
(45) Date of Patent: Oct. 15, 2024

(54) INFLATABLE SLEEVE MULTI-ELECTRODE CATHETER

(71) Applicant: Biosense Webster (Israel) Ltd., Yokneam (IL)

(72) Inventor: Assaf Govari, Haifa (IL)

(73) Assignee: Biosense Webster (Israel) Ltd., Yokneam (IL)

(*) Notice: Subject to any disclaimer, the term of this patent is extended or adjusted under 35 U.S.C. 154(b) by 580 days.

(21) Appl. No.: 17/017,206

(22) Filed: Sep. 10, 2020

(65) Prior Publication Data

US 2021/0113263 A1 Apr. 22, 2021

Related U.S. Application Data (60) Provisional application No. 62/924,394, filed on Oct. 22, 2019.

(51) Int. Cl.
*A61B 18/14* (2006.01)
*A61B 18/00* (2006.01)

(52) U.S. Cl.
CPC ..... *A61B 18/1492* (2013.01); *A61B 2018/00059* (2013.01); *A61B 2018/00214* (2013.01); *A61B 2018/00577* (2013.01); *A61B 2018/1405* (2013.01); *A61B 2018/1467* (2013.01)

(58) Field of Classification Search
CPC ...... A61B 18/1492; A61B 2018/00059; A61B 2018/00214; A61B 2018/00577; A61B 2018/1405; A61B 2018/1467; A61B 2018/00375; A61B 2018/1407; A61B 2018/144; A61B 2018/1497
See application file for complete search history.

(56) References Cited

U.S. PATENT DOCUMENTS

| | | | |
|---|---|---|---|
| 5,499,981 A | 3/1996 | Kordis | |
| 5,700,262 A | 12/1997 | Acosta et al. | |
| 6,371,955 B1 | 4/2002 | Fuimaono et al. | |
| 6,592,581 B2 | 7/2003 | Bowe | |

(Continued)

FOREIGN PATENT DOCUMENTS

| CN | 108882961 A | 11/2018 |
|---|---|---|
| JP | 2010000370 A | 1/2010 |

(Continued)

OTHER PUBLICATIONS

Extended European Search Report dated Mar. 19, 2021, from corresponding European Application No. 20203141.5.

(Continued)

*Primary Examiner* — Adam Z Minchella
(74) *Attorney, Agent, or Firm* — Troutman Pepper Hamilton Sanders LLP (57) ABSTRACT

An apparatus includes a shaft and an inflatable sleeve catheter. The shaft is configured for insertion through a sheath into a cavity of an organ of a patient. The inflatable sleeve catheter is fixed to a distal end of the shaft, with the inflatable sleeve catheter including (i) a resilient inner end section, which is fixed to the distal end of the shaft and is formed so as to assume a predefined shape when unconstrained, (ii) an inflatable sleeve that envelopes the inner end section, and a plurality of electrodes that are disposed over the inflatable sleeve and are configured to contact tissue.

13 Claims, 4 Drawing Sheets

(56) References Cited

U.S. PATENT DOCUMENTS

| | | | |
|---|---|---|---|
| 6,723,094 B1 | 4/2004 | Desinger | |
| 8,456,182 B2 | 6/2013 | Bar-Tal et al. | |
| 8,600,472 B2 | 12/2013 | Govari et al. | |
| 8,900,214 B2 | 12/2014 | Nance et al. | |
| 9,289,606 B2 | 3/2016 | Paul et al. | |
| 2003/0069570 A1* | 4/2003 | Witzel | A61B 18/1492 606/41 |
| 2003/0153905 A1* | 8/2003 | Edwards | A61B 18/1492 606/41 |
| 2004/0106920 A1 | 6/2004 | Jenkins et al. | |
| 2004/0167509 A1* | 8/2004 | Taimisto | A61B 18/1492 606/41 |
| 2004/0215186 A1* | 10/2004 | Cornelius | A61M 25/0082 606/41 |
| 2005/0004566 A1 | 1/2005 | Taimisto | |
| 2006/0089634 A1* | 4/2006 | Anderson | A61B 18/1492 606/41 |
| 2011/0152855 A1 | 6/2011 | Mayse et al. | |
| 2013/0165990 A1* | 6/2013 | Mathur | A61N 1/06 607/101 |
| 2015/0141982 A1 | 5/2015 | Lee | |
| 2016/0175041 A1 | 6/2016 | Govari et al. | |
| 2019/0314610 A1* | 10/2019 | Laduca | A61M 25/0147 |

FOREIGN PATENT DOCUMENTS

| | | |
|---|---|---|
| JP | 2013508121 A | 3/2013 |
| WO | 2017174387 A1 | 10/2017 |

OTHER PUBLICATIONS

English translation of Notice of Reasons for Refusal dated Mar. 26, 2024, from corresponding Japanese Application No. 2020-176493.

English translation of Search Report dated Mar. 27, 2024, from corresponding Japanese Application No. 2020-176493.

English translation of Written Opinion dated Jun. 20, 2024, from corresponding Japanese Application No. 2020-176493.

English translation of Decision to Grant a Patent dated Jul. 2, 2024, from corresponding Japanese Application No. 2020-176493.

* cited by examiner

INFLATABLE SLEEVE MULTI-ELECTRODE CATHETER

CROSS-REFERENCE TO RELATED APPLICATIONS

This application claims the benefit of U.S. Provisional Patent Application 62/924,394, filed Oct. 22, 2019, whose disclosure is incorporated herein by reference as if set forth in full herein.

FIELD OF THE INVENTION

The present invention relates generally to medical probes, and particularly to cardiac electro-anatomical mapping and ablation catheters.

BACKGROUND OF THE INVENTION

Multi-electrode cardiac catheters were previously proposed in the patent literature. For example, U.S. Pat. No. 9,289,606 describes catheter systems that include direction-sensitive, multi-polar tip electrode assemblies, including configurations for producing narrow, linear lesions as well as distributed, wide area lesions. In an embodiment, the electrode elements are distributed contiguously in a linear or arcuate fashion on an outermost surface of a tubular base structure. The tubular base structure comprises electrically-nonconductive material.

As another example, U.S. Pat. No. 8,600,472 describes cardiac catheters, including a lasso catheter, for use in a system for electrical mapping and ablation of the heart. The lasso catheter has an array of raised, circumferential ring bump electrodes wherein each circumferential electrode has multiple perforations, which are in fluid communication with a cavity or chamber formed under the surface of the circumferential ring. The cavity is formed 360 degrees around the outer surface or loop lumen of the lasso segment of the catheter which is in fluid communication with a breach hole (or holes) drilled through loop lumen and in fluid communication with an irrigating lumen.

Pulmonary vein (PV) isolation procedures often apply ablation to induce circumferential lesions at an ostium of a PV for the purpose of eliminating unwanted electrical pathways that may cause arrhythmia. For example, U.S. Patent Application Publication 2016/0175041 describes cardiac ablation that is carried out by introducing a catheter into the left atrium, extending a lasso guide through the lumen of the catheter to engage the wall of a PV, and deploying a balloon over the lasso guide. The balloon has an electrode assembly disposed its exterior. The electrode assembly includes a plurality of ablation electrodes circumferentially arranged about the longitudinal axis of the catheter. The inflated balloon is positioned against the PV ostium, so that the ablation electrodes are in galvanic contact with the PV, and electrical energy is conducted through the ablation electrodes to produce a circumferential lesion that circumscribes the PV.

SUMMARY OF THE DISCLOSURE

An embodiment of the present invention that is described hereinafter provides an apparatus including a shaft and an inflatable sleeve catheter. The shaft is configured for insertion through a sheath into a cavity of an organ of a patient. The inflatable sleeve catheter is fixed to a distal end of the shaft, with the inflatable sleeve catheter including (i) a resilient inner end section, which is fixed to the distal end of the shaft and is formed so as to assume a predefined shape when unconstrained, (ii) an inflatable sleeve that envelopes the inner end section, and a plurality of electrodes that are disposed over the inflatable sleeve and are configured to contact tissue.

In some embodiments, the resilient inner end section is straight. In other embodiments, the inflatable sleeve catheter is deflectable.

In some embodiments, the electrodes have a cylinder shape. In other embodiments, the electrodes have a hemi-cylinder shape.

In an embodiment, the inflatable sleeve catheter is a lasso catheter, and the resilient inner end section is formed so as to assume an arcuate shape when unconstrained, and wherein the plurality of electrodes is circumferentially disposed over the inflatable sleeve.

In another embodiment, the inner end section is made at least partially of a shape memory alloy having a self-configurable pre-formed shape including a straight base segment and an arcuated segment parts. In yet another embodiment, the inflatable sleeve envelopes the inner end section by being threaded by the inner end section along the straight base segment and an arcuated segment parts of the inner end section.

In some embodiments, the inner end section turns unconstrained when exiting the sheath.

In some embodiments, the inflatable sleeve is configured to be inflated using saline solution.

In an embodiment, the apparatus further includes a flexible PCB sheet having the plurality of electrodes disposed thereon.

In another embodiment, the flexible PCB sheet is glued to the inflatable sleeve.

There is additionally provided, in accordance with another embodiment of the present invention, a method including inserting into a cavity of an organ of a patient, through a sheath, an inflatable sleeve catheter fixed to a distal end of a shaft, the inflatable sleeve catheter including (i) a resilient inner end section, which is fixed to the distal end of the shaft and is formed so as to assume a predefined shape when unconstrained, (ii) an inflatable sleeve that envelopes the inner end section, and (iii) a plurality of electrodes that are disposed over the inflatable sleeve and are configured to contact tissue. After the inflatable sleeve catheter exits the sheath in the cavity and the resilient inner end section assumes the predefined shape, the inflatable sleeve is inflated, and contact is made between the plurality of electrodes and tissue, and performing a medical procedure using the electrodes.

There is further provided, in accordance with another embodiment of the present invention, a method of manufacturing an inflatable sleeve catheter, the method including fixing to a distal end of a shaft a resilient inner end section, which is formed so as to assume, when unconstrained, a predefined shape. The inner end section is enveloped with an inflatable sleeve. A plurality of electrodes is disposed over an outer circumference of the inflatable sleeve, that are configured to contact tissue.

The present invention will be more fully understood from the following detailed description of the embodiments thereof, taken together with the drawings in which:

DETAILED DESCRIPTION OF EMBODIMENTS

Overview

Distal ends of diagnostic and/or therapeutic catheters for cardiac applications, such as arcuated distal ends or distal ends that have a deflectable shape (e.g., piecewise linear shape), or have a rigid linear shape, conventionally take their shape from a resilient end section, which is fixed to the distal end of a shaft, and which is formed to assume a predefined (e.g., an arcuate, or straight) shape when unconstrained. In case of an arcuate shape, the arcuate shape should enable, in principle, electrodes disposed over the arcuate end section to engage some or all of the circumference of an opening in the heart, such as an ostium of a pulmonary vein (PV). In case of linear distal ends, the distal end may be deflected to fit variable anatomy (e.g., a septum) to enable some or all of the electrodes disposed over the deflectable distal end to engage the target cardiac tissue.

However, a resilient distal section, such as an arcuate one or a linear one, which is made of rigid materials, such as a plastic-coated metal, with a cross-section large enough to support electrodes, may not easily accommodate a variable shape of the opening. As a result, only a portion of the electrodes disposed over the circumference of, for example, the arcuate end section actually comes in contact with tissue, leaving the electrodes not in contact with tissue in the blood pool. Thus, when the electrodes are used for acquisition of electrophysiological signals from tissue, unwanted electrophysiological signals from the blood interfere. When the electrodes are used for tissue ablation, electrical power is injected into the blood, which may cause side effects such as blood clots.

Similarly, linear rigid distal ends and even deflectable ones, may not easily accommodate a variable shape of an anatomy (e.g., chamber wall tissue).

Moreover, even electrodes that do contact tissue may, due to the rigidity of the arcuate end section, be only in partial contact with tissue, e.g., with a significant portion of electrode area still in contact with blood pool. Such electrodes may also give unwanted electrophysiological signals and may contribute to side effects of an ablation.

Embodiments of the present invention that are described hereinafter provide a catheter comprising an inflatable sleeve that envelopes a thin inner end section, which, when unconstrained, takes a predefined shape, such as an arcuate shape. The disclosed inner end section, which is also called hereinafter the "wire former," threads the inflatable sleeve through the entire length of the sleeve. The disclosed wire former gives the sleeve its predefined (e.g., arcuate, linear) shape and serves as a rigid "backbone," whereas the inflatable sleeve gives the catheter the needed balance between extra structural stiffness and tissue accommodative properties. For example, the stiffness of the inflatable sleeve can be tuned by adjusting the rate of saline solution that is pumped into the sleeve to maintain the sleeve's inflation. As another example, the thickness of the sleeve and/or the plastic type used for the sleeve construction can be selected to give the optimized balance.

In some embodiments, multiple electrodes are disposed circumferentially and equidistantly over the entire outer circumferential, or elongated, surface of the inflatable sleeve. Due to its inherent capability to accept anatomy shape while maintaining sufficient resilience, the cross-sectional diameter of the disclosed inflatable sleeve catheter can be made large enough to support large-area electrodes, which can still be brought into full contact with tissue.

In a typical procedure, the inflatable catheter, which is fixed to the distal end of a shaft, is advanced through a sheath by a physician into a desired body location, such as the left atrium, with the wire former straightened by a sheath. In case of an inflatable lasso catheter, once the lasso emerges out of the sheath into the left atrium, the wire former resumes its unconstrained arcuate form. The physician then inflates the sleeve and maneuvers the catheter to establish contact between the electrodes disposed on the sleeve and tissue, such as of an ostium. When the diagnostic and/or therapeutic procedure ends, the physician deflates the lasso, and withdraws the deflated lasso catheter through the sheath. The withdrawal process is typically made easier by using a thin wire former.

In some embodiments, the electrodes (with their electrical connections) are formed on an electrode support, which is typically a flexible PCB sheet, and the support is glued to the inflatable sleeve. In some embodiments of the inflatable lasso catheter, the electrodes are disposed on the outer (tissue-facing) circumference of the inflatable sleeve, and are not fully cylindrical, i.e., do not fully surround the inflatable sleeve to reach the inner circumference that faces away from the tissue. This configuration helps minimizing unnecessary exposure of the electrodes to blood. The accommodating properties of the inflatable sleeve, together with electrode shape and location, thus assist in minimizing unwanted interference from stray electrophysiological signals and ejection of electrical power to blood.

As noted above, the disclosed inflatable sleeve can support large-area electrodes, which can be, for example, glued to the sleeve. Large-area electrodes can clinically outperform small electrodes, for example, by creating larger lesions. Furthermore, large electrodes are more resilient to being scraped off when the catheter is pushed against an ostium wall tissue so the electrodes can come in firm contact with tissue.

The disclosed inflatable sleeve catheter may have superior diagnostic and therapeutic capabilities (e.g., relative to other types of catheters such as balloon catheters) and its use may increase the rate of successful and safe ablation treatments of severe cardiac conditions, such as drug-resistant arrhythmia.

System Description

Figure 1:
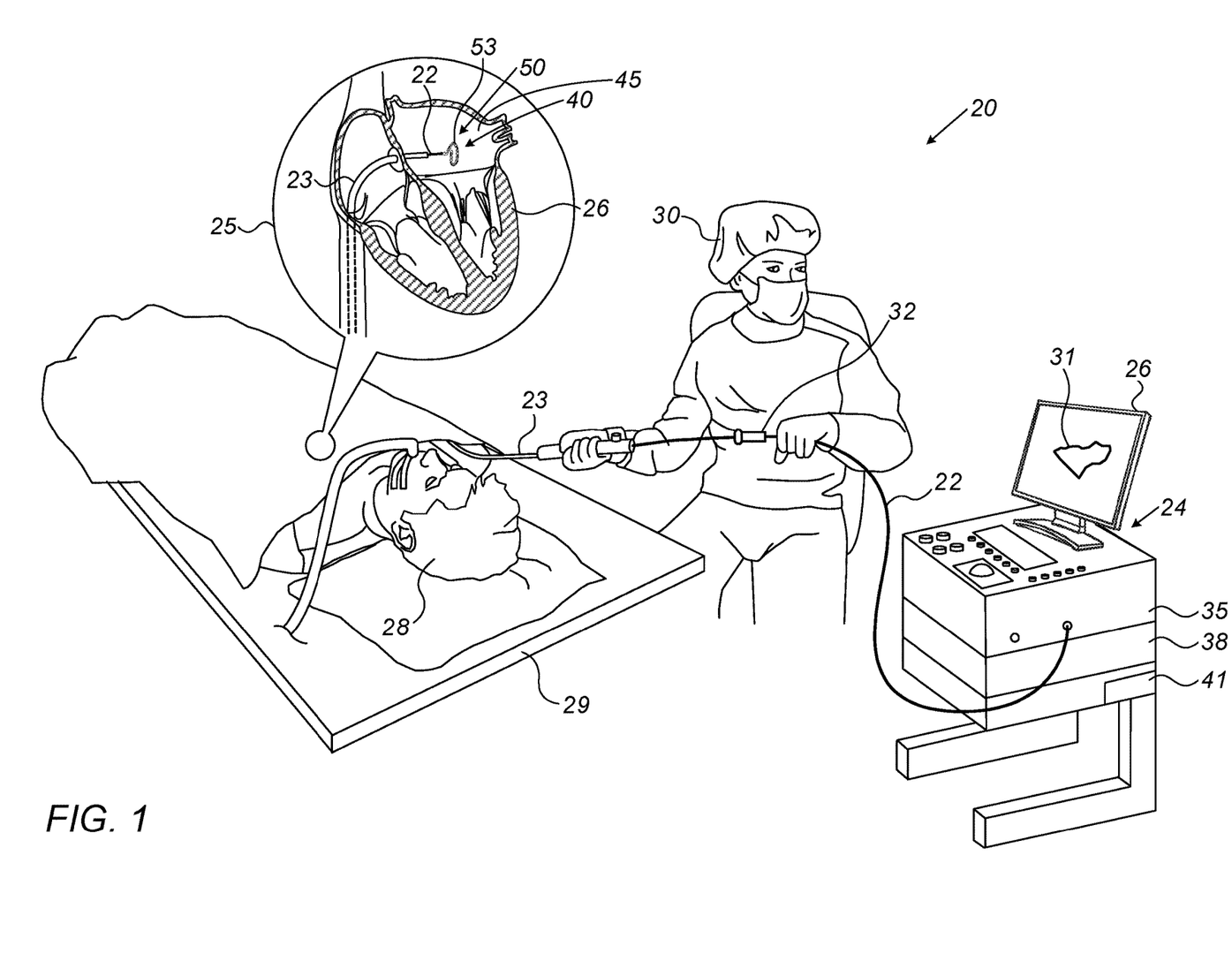
FIG. 1 is a schematic, pictorial illustration of a system for electro-anatomical mapping and ablation, in accordance with an embodiment of the present invention.

FIG. 1 is a schematic, pictorial illustration of a system 20 for electro-anatomical mapping and ablation, in accordance with an embodiment of the present invention. As seen, inflatable sleeve lasso catheter 40 is fitted at the distal end of a shaft 22 that is inserted through a shaft 23 into a heart 26 of a patient 28 on a table 29. FIG. 1 depicts a physician 30 using an inflatable sleeve lasso catheter 40 to perform an electro-anatomical mapping of a cardiac chamber, such as a left atrium 45 of heart 26. Inset 25 further shows inflatable sleeve lasso catheter 40 disposed with multiple electrodes 53.

Figure 2:
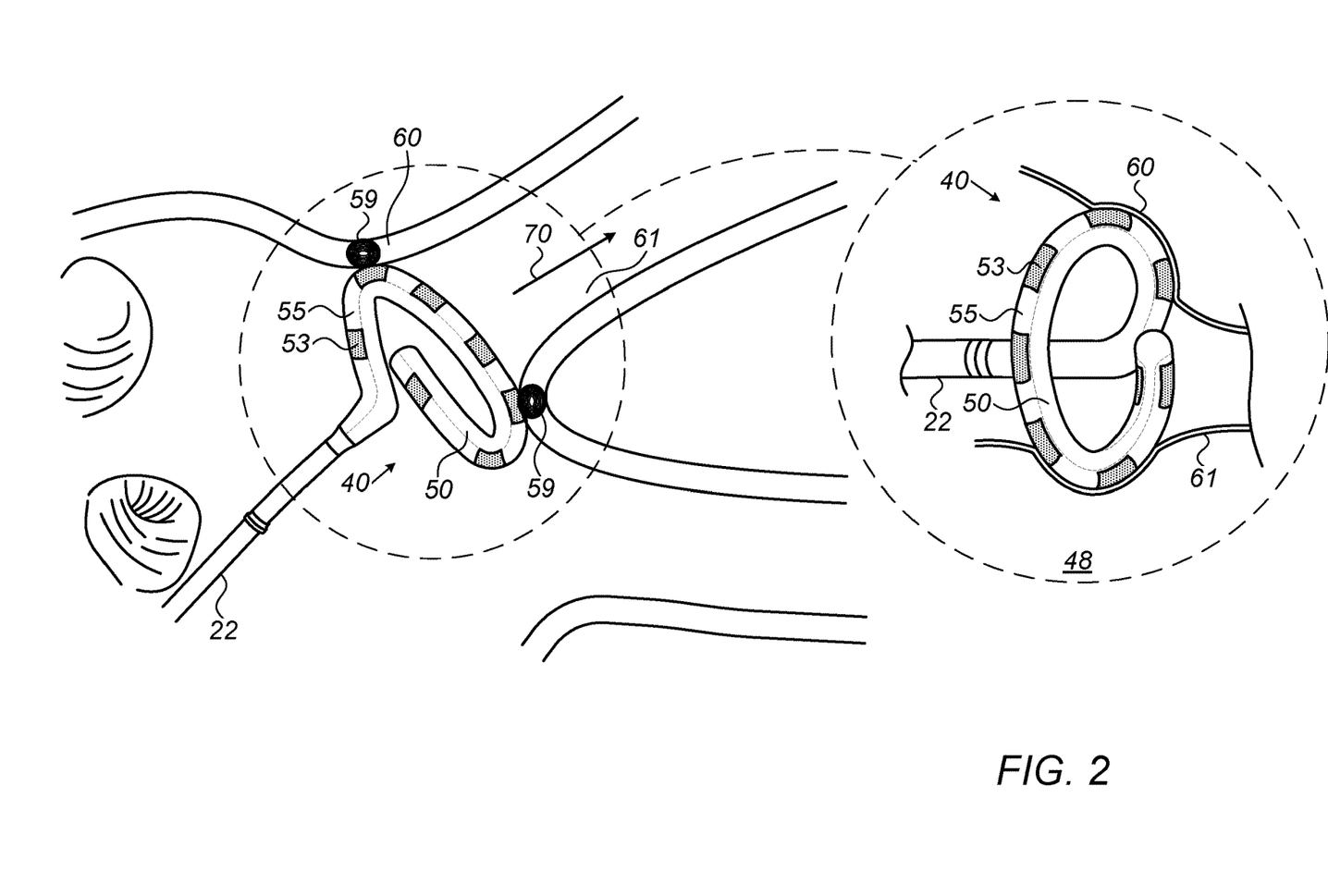
FIG. 2 is a schematic, pictorial illustration of the distal portion of the inflatable sleeve lasso catheter shown in FIG. 1 in an operating position for electro-anatomical sensing and ablation, in accordance with an embodiment of the invention.
Figure 3:
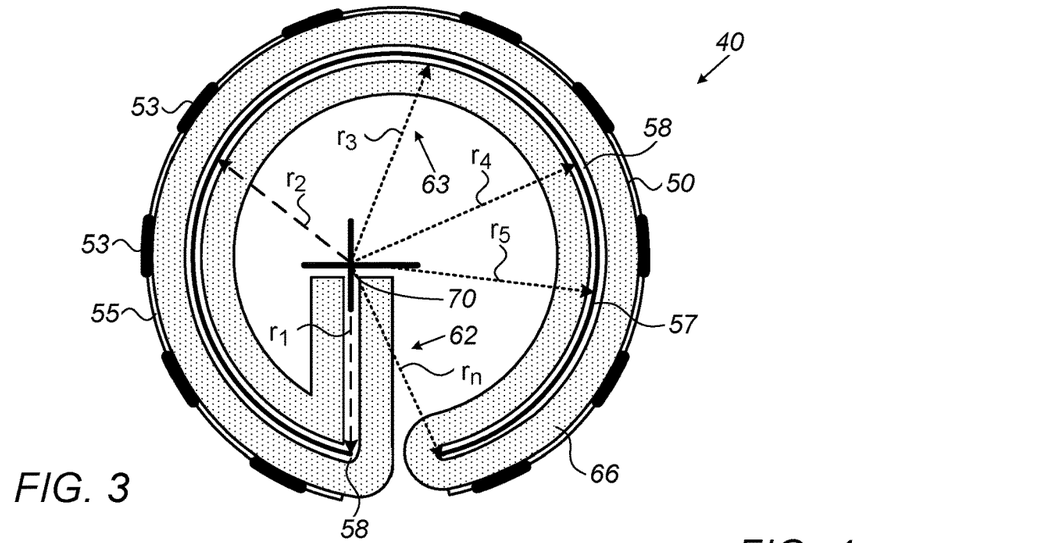
FIG. 3 is a schematic cross-section of the inflatable sleeve lasso catheter of FIG. 2, in accordance with an embodiment of the invention.

Once the distal end of shaft 22 has reached target location (e.g., left atrium 45), physician 30 retracts sheath 23, and catheter 40 takes a lasso shape due to the wire former, shown in FIG. 3, self-expanding into its pre-formed arcuate shape. Next, physician 30 inflates a sleeve 50 by pumping saline solution into sleeve 50. Physician 30 further manipulates shaft 22 to place electrodes 53 disposed over a perimeter of sleeve 50 in contact with tissue, such as with an ostium of a PV, as seen in FIG. 2.

During a mapping procedure, electrodes 53 acquire and/or inject signals from and/or to the tissue of left atrium 45. A processor 38 in console 24 receives these signals via an electrical interface 35, and uses information contained in these signals to construct an electro-anatomical map 31. During and/or following the procedure, processor 38 may display electro-anatomical map 31 on a display 26. Typically, processor 38 stores electro-anatomical map 31 in memory 41.

Physician 30 navigates the distal end of a shaft 22 to a target location inside left atrium 45 of heart 26 by manipulating shaft 22 using a manipulator 32 near the proximal end of the catheter and/or deflection from sheath 23. During the insertion of shaft 22, inflatable sleeve lasso catheter 40 is maintained in a collapsed configuration by sheath 23. By containing catheter 40 in a collapsed configuration, sheath 23 also serves to minimize vascular trauma along the way to the target location.

During the procedure, a tracking system is used to track the respective locations of electrodes 53, such that each of the diagnostic signals may be associated with the location at which the diagnostic signal was acquired. A suitable tracking system is, for example, the Advanced Catheter Location (ACL) system, made by Biosense-Webster (Irvine, California), which is described in U.S. Pat. No. 8,456,182, whose disclosure is incorporated herein by reference. In the ACL system, a processor estimates the respective locations of electrodes 53 based on impedances measured between each of the electrodes, and a plurality of surface-electrodes 49 that are coupled to the skin of patient 28.

The example illustration shown in FIG. 1 is chosen purely for the sake of conceptual clarity. Other tracking methods can be used, such as ones based on measuring voltage signals. In an optional embodiment, processor 38 is further configured to indicate the quality of physical contact between inflatable sleeve lasso catheter 40 an inner surface of left atrium 45 during measurement and/or during ablation.

Processor 38 typically comprises a general-purpose computer with software programmed to carry out the functions described herein. The software may be downloaded to the computer in electronic form, over a network, for example, or it may, alternatively or additionally, be provided and/or stored on non-transitory tangible media, such as magnetic, optical, or electronic memory.

Inflatable Lasso Catheter

FIG. 2 is a schematic, pictorial illustration of the distal portion of inflatable sleeve lasso catheter 40 shown in FIG. 1 in an operating position for radiofrequency ablation, in accordance with an embodiment of the invention. Inflatable sleeve lasso catheter 40 is shown fully inflated and fixed to the distal end of shaft 22. The distal end of shaft 22 defines a longitudinal axis 70 along and parallel to the distal end of shaft 22. The arcuate inner end section (seen in FIG. 3) causes inflated sleeve 50 to spiral about longitudinal axis 70 and at the same time to slightly prograde.

As used herein, the term "arcuate" or "arcuate shape" denotes a shape of an arc segment extending about a longitudinal axis and which arc segment may be bent in a semi-circular segment or elliptical segment as viewed by an observer facing longitudinal axis 70 (as in FIG. 3). The flexible sleeve may define an arcuate shape with a generally constant radii (as measured from axis 70), which can be seen in FIG. 2. Alternatively, in FIG. 3, flexible sleeve may define an arcuate shape that extends in the form of an outward spiral with radii that increase ($r_1, r_2, r_3, r_4, r_5 \ldots r_n$) from axis 70 as viewed by an observer on the axis 70. In certain embodiments, the arc segment can extend less than 90 degrees to over 180 degrees (FIG. 3) and in certain cases up to 720 degrees with respect to the longitudinal axis 70. The arcuate segment may also translate along axis 70 to mimic part of a spiral or helicoid about axis 70.

As seen, a fully inflated sleeve 50 of inflatable sleeve lasso catheter 40 contacts an ostium 60 of a PV 61 over an entire circumference of ostium 60. Inflated sleeve has multiple ablation electrodes 53 disposed on a flexible PCB 55, on an outer surface of sleeve 50. In a PV isolation procedure, passage of electrical energy through electrodes 53 creates a circumferential lesion 59 at ostium 60 that blocks electrical propagation and isolates the PV from the heart. Electrodes 53 are further useful to obtain electrograms to confirm electrical isolation of the PV following ablation.

An inset 48 shows inflatable lasso 40 from a perspective that emphasizes the inherent capability of the combined structure of the wire former and inflatable sleeve 50 to both accept shape of an anatomy while pushing tissue hard enough to have hemi-cylinder-shaped electrodes 53 firmly in contact with ostium 60 tissue over most or an entirety of electrodes 53 area, i.e., with minimal, if any electrode area left exposed to blood.

The example illustration shown in FIG. 2 is chosen purely for the sake of conceptual clarity. For example, other geometrical shapes of electrodes 53 are possible, such as an oval patch.

FIG. 3 is a schematic cross-section of inflatable sleeve lasso catheter 40 of FIG. 2, in accordance with an embodiment of the invention. As seen, sleeve 50 is threaded by a wire former 57 that occupies a circumferential space 58 defined by sleeve 50. Electrodes 53 are disposed on the flexible PCB 55, which is itself disposed over an external outer surface of sleeve 50.

Sleeve 50 is shown fully inflated, e.g., by saline solution 66, which is pumped via a lumen (not shown) that goes inside shaft 22 and is in fluid connection with sleeve 50.

In an embodiment, wire former 57 is made at least partially of a shape memory alloy having a self-configurable pre-formed shape comprising straight base segment 62 and arcuated segment 63 parts. Thus, when physician 30 advances catheter 40 beyond a distal edge of sheath 23, wire former 57 turns unconstrained and as a result self-configures from a collapsed straight configuration into an expanded configuration having straight base segment 62 and arcuated segment 63 parts.

The example illustration shown in FIG. 3 is chosen purely for the sake of conceptual clarity. FIG. 3 only shows parts relevant to embodiments of the present invention. Other details, such as irrigation holes, temperature sensors, and electrical wiring are omitted for simplicity of presentation.

Figure 4:
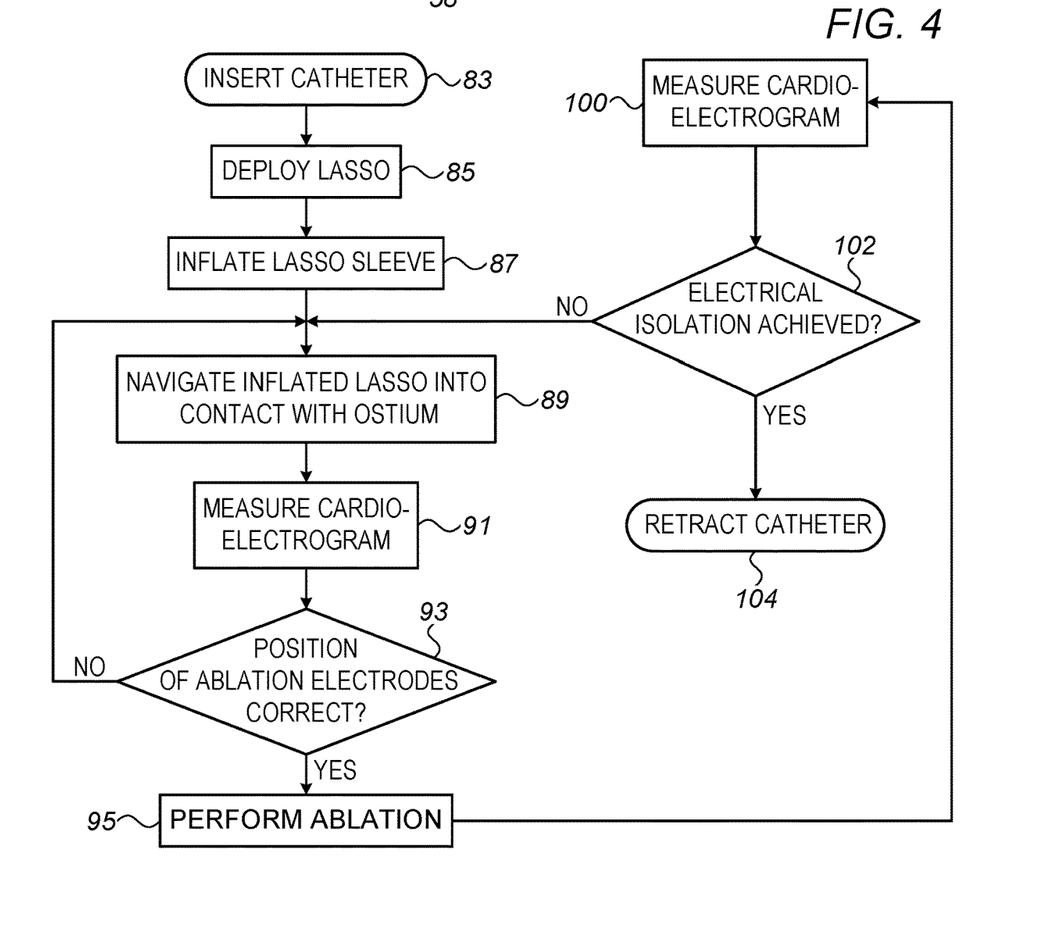
FIG. 4 is a flow chart that schematically illustrates a method for pulmonary vein (PV) isolation using the inflatable sleeve lasso catheter of FIG. 2, in accordance with an embodiment of the invention.

FIG. 4 is a flow chart that schematically illustrates a method for pulmonary (PV) vein isolation, in accordance with an embodiment of the invention. The procedure may begin with physician 30 inserting inflatable sleeve lasso catheter 40 into the left atrium of a heart, at an insertion step 83.

Next, at a deployment step 85, physician 30 deploys catheter 40 out of sheath 23 in the vicinity of the interior wall of ostium 60, letting wire former 57 take its preformed shape. Next, at an inflation step 87, physician 30 inflates sleeve 50. At a positioning step 89, physician 30 brings the inflatable lasso catheter into circumferential contact with ostium 60 of PV 61, which brings electrodes 53 into firm contact with ostium 60 wall tissue. Once inflatable lasso catheter 40 is in position, pre-ablation cardio-electrograms are acquired by physician 30, at a measurement step 91.

The method now proceeds to a decision step 93, in which physician 30 determines, based on the electrograms, whether electrodes 53 are correctly positioned. If the determination at decision step 93 is negative, then the method returns to step 89 and physician 30 may reattempt to optimally position inflatable lasso catheter 40.

If the determination at decision step 93 is affirmative, then the method proceeds to an ablation step during which physician 30 performs ablation using electrodes 53. The ablation operation creates circumferential lesion 59 in a region of tissue that circumscribes ostium 60. Lesion 59 should block electrical propagation and effectively electrically isolate PV 61 from the heart. In order to confirm functional isolation of PV 61, post-ablation electrograms are obtained by physician 30 from electrodes 53 of inflatable lasso catheter 40, at measurement step 100.

If analysis of the cardio-electrograms, at a decision step 102, shows that lesion 59 does not fully electrically isolate PV 61 from the heart, then physician 30 may perform another attempt by looping back to positioning step 89.

After completion of the ablation, the procedure may be iterated to treat another PV ostium by withdrawal of the distal end of shaft 22 and thereby of the deflated lasso catheter 40. The method may then return to step 85. Alternatively, physician 30 may end the procedure and retract the catheter from the heart, at a retraction step 104.

The example flow chart shown in FIG. 4 is chosen purely for the sake of conceptual clarity. In alternative embodiments, additional steps may be performed, such applying irrigation to cool ostium 60 tissue.

Inflatable Linear Catheter

By straight forward analogy to the lasso catheter, a sleeve catheter may be implemented for various types of catheter geometries, including a catheter carrying a linear array of electrodes, where the catheter may be rigid or deflectable. While the shown embodiment is of a deflectable distal end, the same description is valid for a straight, linear, distal end.

Figure 5:
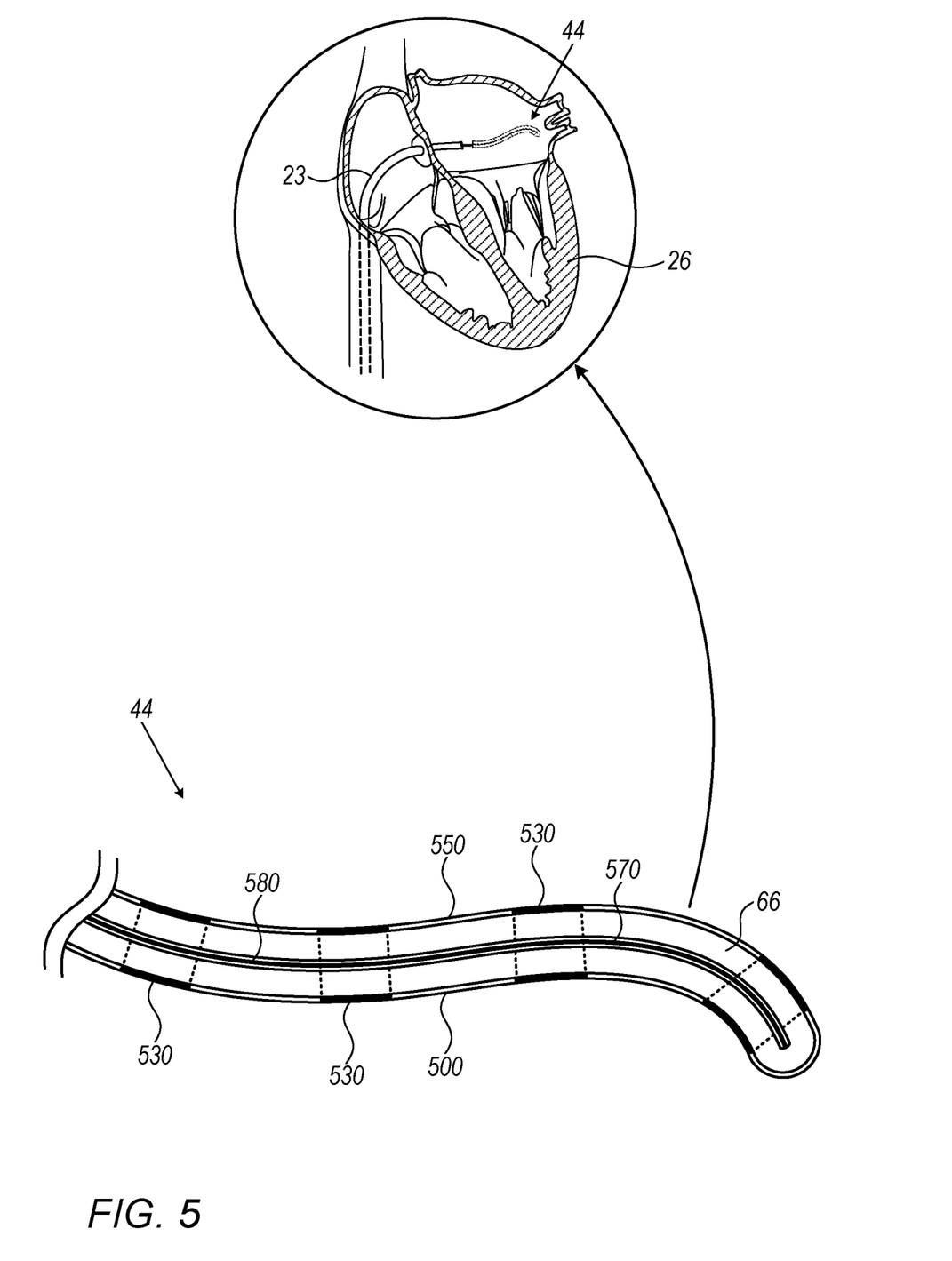
FIG. 5 is a schematic cross-section of an inflatable sleeve deflectable linear catheter, in accordance with an embodiment of the invention.

FIG. 5 is a schematic cross-section of an inflatable sleeve deflectable linear catheter 44, in accordance with an embodiment of the invention.

As seen, a sleeve 500 of catheter 44 is threaded by a deflectable wire former 570 that occupies a space 580 defined by sleeve 500. Wire former 570 may be made by separate links and may include elements to deflect the wire. Alternatively, wire former 570 is made at least partially of a shape memory alloy having a self-configurable pre-formed shape, such as of a straight line. Electrodes 530, which are cylinder shape electrodes, are disposed on a flexible PCB 550, which is itself disposed over an external outer surface of sleeve 500.

Sleeve 500 is shown fully inflated, e.g., by saline solution 66, which is pumped via a lumen (not shown) that goes inside a shaft of the catheter and is in fluid connection with sleeve 500.

The example illustration shown in FIG. 5 is chosen purely for the sake of conceptual clarity. FIG. 5 only shows parts relevant to embodiments of the present invention. Other details, such as deflection elements, irrigation holes, temperature sensors, and electrical wiring are omitted for simplicity of presentation.

The lasso, straight, and deflectable catheters embodiments described above were brought by way of example. The disclosed inflatable sleeve may be used with any shape of an inner end section, such as, as another example, of a multi-arm catheter.

Although the embodiments described herein mainly address the disclosed inflatable lasso, straight, and deflectable catheters in relation with cardiac diagnostic and therapeutic applications, the methods and systems described herein can also be used in other applications, such in neurology and otolaryngology.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. An apparatus, comprising:
   a shaft configured for insertion through a sheath into a cavity of an organ of a patient; and
   an inflatable sleeve catheter fixed to a distal end of the shaft, the inflatable sleeve catheter comprising:
      a resilient inner end section, which is fixed to the distal end of the shaft and is formed so as to assume a predefined shape when unconstrained, the predefined shape comprising a straight base segment and an arcuated segment;
      an inflatable sleeve that envelopes the resilient inner end section from a distal end of the shaft, along the straight base segment, and along the arcuated segment to a distal end of the apparatus; and
      a plurality of electrodes that are disposed over the inflatable sleeve and are configured to contact tissue.

2. The apparatus according to claim 1, wherein the inflatable sleeve catheter is deflectable.

3. The apparatus according to claim 1, wherein the electrodes have a cylinder shape.

4. The apparatus according to claim 1, wherein the electrodes have a hemi-cylinder shape.

5. The apparatus according to claim 1, wherein the inflatable sleeve catheter is a lasso catheter, wherein the resilient inner end section is formed so as to assume an arcuate shape comprising the arcuated segment when unconstrained, and wherein the plurality of electrodes is circumferentially disposed over the inflatable sleeve.

6. The apparatus according to claim 5, wherein the resilient inner end section is made at least partially of a shape memory alloy having a self-configurable pre-formed shape comprising the straight base segment and the arcuated segment.

7. The apparatus according to claim 6, wherein the inflatable sleeve envelopes the resilient inner end section by being threaded by the inner end section along the straight base segment and an arcuated segment of the inner end section.

8. The apparatus according to claim 1, wherein the resilient inner end section turns unconstrained when exiting the sheath.

9. The apparatus according to claim 1, wherein the inflatable sleeve is configured to be inflated using saline solution.

10. The apparatus according to claim 1, and comprising a flexible PCB sheet having the plurality of electrodes disposed thereon.

11. The apparatus according to claim 10, wherein the flexible PCB sheet is glued to the inflatable sleeve.

12. The apparatus of claim 1, the arcuated segment comprising an outward spiral form with an increasing radius, relative to a longitudinal axis of the shaft, from a proximal end of the arcuated segment to a distalmost end of the arcuated segment.

13. The apparatus of claim 1, the arcuated segment having a distalmost end, the inflatable sleeve extending beyond and enveloping the distalmost end of the arcuated segment, and the inflatable sleeve being configured to be inflated using a solution such that that the solution envelopes the distalmost end of the arcuated segment.

\* \* \* \* \*